United States Patent [19]

Goel

[11] Patent Number: 4,469,636

[45] Date of Patent: Sep. 4, 1984

[54] MANUFACTURE OF ANTIMONY (III) CARBOXYLATES

[75] Inventor: Anil B. Goel, Worthington, Ohio

[73] Assignee: Ashland Oil, Inc., Ashland, Ky.

[21] Appl. No.: 471,409

[22] Filed: Mar. 2, 1983

[51] Int. Cl.³ .............................. C07F 9/90; C11C 1/00
[52] U.S. Cl. ...................................... 260/414; 260/446
[58] Field of Search ................................. 260/446, 414

[56] References Cited

U.S. PATENT DOCUMENTS

| | | | |
|---|---|---|---|
| 2,335,585 | 11/1943 | Davies | 260/446 |
| 2,528,803 | 11/1950 | Unkefer | 260/414 X |
| 2,996,528 | 8/1961 | Marks et al. | 260/446 |
| 3,211,768 | 10/1965 | Considine | 260/414 |
| 3,415,860 | 12/1968 | Thomas | 260/446 |
| 3,476,786 | 11/1969 | Lally et al. | 260/414 X |
| 3,484,410 | 12/1969 | Lazarus et al. | 260/414 X |
| 4,337,208 | 6/1982 | Petronella | 260/446 X |

*Primary Examiner*—Helen M. S. Sneed
*Attorney, Agent, or Firm*—John F. Jones

[57] ABSTRACT

A process for converting antimony metal to an antimony (III) carboxylate by reaction with a carboxylic acid in the presence of at least one member selected from the group consisting of $HNO_3$, $NO_2$, NO plus $O_2$, NOOCOR and $HNO_2$ is described.

8 Claims, No Drawings

MANUFACTURE OF ANTIMONY (III) CARBOXYLATES

This invention relates to the method for preparing antimony(III) salts of carboxylic acids and more particularly pertains to a novel process for the production of compounds conforming to the formula $Sb(OCOR)_3$ wherein R is a hydrocarbon group or a halogenated hydrocarbon group having from 1 to 19 carbon atoms. These compounds are prepared by the reaction of antimony metal with the carboxylic acid or its anhydride in the presence of a member selected from the group consisting of nitric acid, $NO_2$, NO plus $O_2$, NOOCOR and $HNO_2$ wherein R has the foregoing designation.

Antimony carboxylates, generally $Sb(OAc)_3$, are usually prepared by the reaction of Antimony(III) oxide ($Sb_2O_3$) with acetic acid and acetic anhydride [U.S. Pat. No. 3,415,860 and Ohio J. SCi., 77, 134(1977)]. The direct reaction of antimony metal with carboxylic acids or their anhydrides to form antimony(III) carboxylates has not been reported previously.

Antimony carboxylates such as $Sb(OAc)_3$ have been described in the literature as being catalysts for polyester manufacture by condensation (U.S. Pat. Nos. 3,844,976 and 3,899,522). Antimony carboxylates are also known to be useful as co-catalysts in palladium catalyzed acyloxylation reactions.

In the palladium catalyzed acyloxylation reactions the $Sb(OAc)_3$ sometimes used as co-catalyst often undergoes some reduction to antimony metal in both the liquid phase and vapor phase systems (see U.S. Pat. Nos. 3,959,352 and 3,959,355). When this happens the antimony metal has to be converted back to the respective antimony(III) carboxylate for reuse in the acyloxylation process.

I have discovered a novel, one-step process for converting the antimony metal resulting from the reduction of the antimony carboxylate back to the carboxylate which does not involve use of an antimony oxide intermediate.

This invention provides a convenient process for converting antimony metal to antimony(III) carboxylates which involves allowing antimony metal to react with an excess of a carboxylic acid and usually some of the corresponding carboxylic acid anhydride at a temperature ranging from about 40° C. to 120° C. in the presence of catalytic amounts of at least one member selected from the group consisting of $HNO_3$, $NO_2$, and NO plus $O_2$. Reaction times under these conditions can vary from a few minutes to several hrs. I have observed that in the absence of at least one of these catalytic materials the antimony metal will not react with the carboxylic acid-anhydride even at temperatures up to 120° C. It is usually desirable to include some of the carboxylic acid anhydride in the reaction mixture in the process of my invention because some water is generated in the process and this is used up to converting the anhydride to more of the carboxylic acid. If the water is not removed as it forms it will react with at least some of the antimony(III) carboxylate to cause hydrolysis. The use of the carboxylic acid anhydride is not required, however. The use of heptane or even excess carboxylic acid, which will remove water azeotropically as it forms rather than use of the carboxylic acid anhydride is within the scope of my process. In my process the antimony(III) carboxylates of carboxylic acids conforming to the formula RCOOH wherein R is a hydrocarbon group or a halogenated hydrocarbon group having from 1 to 19 carbon atoms are readily prepared.

The process of this invention is further illustrated in the following representative examples.

EXAMPLE 1

A. To a 250 Ml. round bottom flask equipped with a magnetic stirrer and a condenser, 60 ml. of acetic acid, 5 ml. of acetic anhydride and 1.5 g. of antimony metal (as powder) were charged. This reaction mixture was heated to reflux for 1 hour during which time no change in the antimony metal was observed.

B. The reaction mixture was then cooled to room temperature and 0.35 g. of 70% aqueous $HNO_3$ was added slowly to the stirred mixture. The stirred mixture was then heated to 90° C. and maintained at this temperature for 15 minutes. All of the antimony metal dissolved in this time and the evolution of some brown vapors was observed. The resulting solution was flushed with dry nitrogen to remove the brown vapors and the volatile material was removed at reduced pressure (1 MM Hg at room temperature) to yield an essentially quantitative yield (3.6 grams) of a white crystalline solid (M.P. 133°–134° C.) which showed a U.V. visible spectrum band at about 251 nm in acetic acid and was identified as $Sb(OAc)_3$.

EXAMPLE 2

The procedure of Example 1B was repeated except that 1 g. of antimony metal, 50 ml of acetic acid, 5 ml of acetic anhydride, 0.5 g of $HNO_3$, a reaction temperature of 80° C. and a reaction time of 5 minutes were used. A quantitative yield of $Sb(OAc)_3$ was obtained.

EXAMPLE 3

Apparatus described in Example 1 was used. The reaction mixture was composed of 0.3 g. of antimony metal, 40 ml of glacial acetic acid and 0.35 g. of $HNO_3$. The mixture was heated at 100° C. for about 5 minutes until a clear solution resulted. The acetic acid was removed rapidly by distillation under reduced pressure to avoid causing the precipitation of hydrolyzed $Sb(OAc)_3$. A near quantitative yield of $Sb(OAc)_3$ was obtained.

EXAMPLE 4

A repeat of Example 1B except that no acetic anhydride was used caused the formation of a white insoluble solid. When 20 ml of acetic anhydride was then added and the volatiles were slowly removed from the reaction the insoluble solid slowly dissolved and a near quantitative yield of white crystalline $Sb(OAc)_3$ resulted.

EXAMPLE 5

To a glass flask equipped with a Dean-Stark trap collector and condenser were added 1 g. of powdered antimony metal, 60 ml. of glacial acetic acid and 15 ml of n-heptane. This mixture was refluxed and 0.5 g. of $HNO_3$ was added dropwise. During this addition period (30 minutes) the heptane was distilled off slowly to remove water as it formed from the reaction mixture. The antimony metal dissolved in this time and a quantitative yield of $Sb(OAc)_3$ was produced upon removal of the volatile material from the reaction mixture.

EXAMPLE 6

The procedure of Example 5 was followed using a reaction mixture composed of 1 g. of antimony metal, 50 g. of octanoic acid, 20 ml. of n-heptane and 0.45 g. of 70% aqueous $HNO_3$. The reaction temperature was about 120° C. and the $HNO_3$ was added dropwise as in Example 5. The water of reaction was removed azeotropically with n-heptane and was collected in the Dean-Stark tube as in Example 6. The clear solution which resulted was concentrated and dried to produce a quantitative solid residue of Antimony(III) octanoate which had an UV-visible spectrum band at about 297 nm.

EXAMPLE 7

The procedure of Example 1B was followed using a reaction mixture composed of 0.2 g. of antimony, 30 g. of trifluoroacetic acid, 5 g. of trifluoroacetic anhydride and 0.29 of $HNO_3$. The reaction was carried out at 40°-50° C. for 30 minutes during which time a clear solution formed. Removal of all volatiles afforded a quantitative yield of $Sb(OCOCF_3)_3$ which was a white crystalline solid melting at 114°-116° C.

EXAMPLE 8

The procedure of Example 1B was followed using a reaction mixture composed of 0.2 g. of antimony metal powder, 30 g. of acetic acid and 5 g. of acetic anhydride. A slow stream of $NO_2$ gas was bubbled through the reaction mixture and the reaction temperature was maintained at 80°-90° C. with continuous stirring for 30 minutes during which time most of the antimony dissolved. The reaction mixture was then flushed with dry nitrogen and the volatiles were removed to yield the solid $Sb(OAc)_3$.

I claim:

1. The process for preparing an antimony (III) Carboxylate consisting of allowing a reaction mixture of antimony metal, a carboxylic acid conforming to the formula RCOOH wherein R is A hydrocarbon group or a halogenated hydrocarbon group having from 1 to 19 carbon atoms and at least one member selected from the group consisting of $HNO_3$, $NO_2$, NO plus $O_2$, NOOCOR and $HNO_2$ wherein R has the foregoing designation to react at a temperature in the range of from about 40° C. to 120° C., removing the water of reaction and recovering the solid antimony (III) carboxylate from the mixture.

2. The process of claim 1 wherein some acid anhydride is included in the reaction mixture to remove the water of reaction as it forms.

3. The process of claim 1 wherein the carboxylic acid is acetic acid.

4. The process of claim 1 wherein the carboxylic acid is octanoic acid.

5. The process of claim 1 wherein the carboxylic acid is trifluoroacetic acid.

6. The process of claim 1 wherein $HNO_3$ is used.

7. The process of claim 1 wherein $NO_2$ is used.

8. The process of claim 1 wherein heptane is included in the reaction mixture and the water of reaction is removed azeotropically with heptane.

* * * * *